United States Patent [19]

Krämer et al.

[11] Patent Number: 4,771,065
[45] Date of Patent: Sep. 13, 1988

[54] FUNGICIDAL NOVEL SUBSTITUTED PHENETHYL-TRIAZOLYL DERIVATIVES

[75] Inventors: Wolfgang Krämer; Hans-Joachim Knops, both of Wuppertal; Karl H. Büchel, Burscheid; Paul Reinecke, Leverkusen, all of Fed. Rep. of Germany

[73] Assignee: Bayer Aktiengesellschaft, Leverkusen, Fed. Rep. of Germany

[21] Appl. No.: 589,225

[22] Filed: Mar. 13, 1984

[30] Foreign Application Priority Data

Mar. 24, 1983 [DE] Fed. Rep. of Germany ....... 3310830

[51] Int. Cl.[4] ................... C07D 249/08; A01N 31/41
[52] U.S. Cl. ................... 514/383; 514/184; 548/262; 548/101
[58] Field of Search ................ 548/101, 262; 424/269, 424/245; 514/383, 184

[56] References Cited

U.S. PATENT DOCUMENTS

| 4,124,767 | 11/1978 | Mixich et al. | 548/341 |
| 4,177,350 | 12/1979 | Zirngibl et al. | 548/341 |
| 4,327,104 | 4/1982 | Timmler et al. | 548/262 |
| 4,357,338 | 11/1982 | Krämer et al. | 548/262 |
| 4,360,526 | 11/1982 | Zeeh et al. | 548/341 |

FOREIGN PATENT DOCUMENTS

| 0069289 | 1/1983 | European Pat. Off. | 548/262 |
| 2431407 | 1/1976 | Fed. Rep. of Germany | 548/262 |
| 2023141 | 12/1979 | United Kingdom | 514/399 |

*Primary Examiner*—Glennon H. Hollrah
*Assistant Examiner*—D. L. Dinner
*Attorney, Agent, or Firm*—Sprung Horn Kramer & Woods

[57] ABSTRACT

A fungicidally active substituted phenethyl-triazolyl derivative of the formula

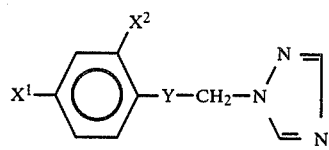

in which
$X^1$ and $X^2$ each independently is halogen or halogenoalkyl, and one of them may also be hydrogen,
Y is $>C{=}N{-}O{-}R$ or $>CH{-}O{-}R$,
R is phenoxyethyl which is optionally substituted in the phenyl part,
or an addition product thereof with an acid or salt.

10 Claims, No Drawings

FUNGICIDAL NOVEL SUBSTITUTED PHENETHYL-TRIAZOLYL DERIVATIVES

The present invention relates to new substituted phenethyl-triazolyl derivatives, a process for their preparation and their use as fungicides.

It has already been disclosed that substituted 1-benzyloximino- or -benzyloxy-1-phenyl-2-triazolyl-ethanes, such as, for example, 1-(4-chlorobenzyl-oximino)-1-(2,4-dichlorophenyl)-2-(1,2,4-triazol-1-yl)-ethane, 1-(2,6-dichlorobenzyloximino)-1-(2,4-dichlorophenyl)-2-(1,2,4-triazol-1-yl)-ethane or 1-(2-chlorobenzyloxy)-1-(2,4-dichlorophenyl)-2-(1,2,4-triazol-1-yl)-ethane, have good fungicidal properties) compare U.S. Pat. Nos. 4,357,338 and 4,327,104).

However, the action of these compounds is not always completely satisfactory, especially when low amounts and concentrations are applied.

New substituted phenethyl-triazolyl derivatives of the general formula

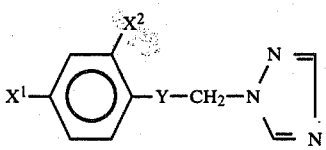

in which
  $X^1$ and $X^2$ are identical or different and represent hydrogen, halogen or halogenoalkyl, but $X^1$ and $X^2$ may not simultaneously represent hydrogen, and
  Y represents the grouping $>C=N-O-R$ or $>CH-O-R$
wherein
  R represents phenoxyethyl which is optionally substituted in the phenyl part,
and acid addition salts and metal salt complexes thereof, have been found.

The compounds of the formula (I) where $R=>C=N-O-R$ can exist in the syn- or anti-form; they are predominantly obtained as mixtures of the two forms.

It has furthermore been found that the substituted phenethyl-triazolyl derivatives of the formula (I) are obtained by a process in which phenethyl-triazolyl derivatives of the formula

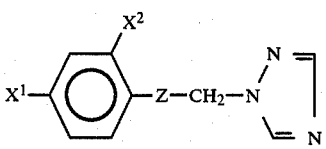

in which
  $X^1$ and $X^2$ have the abovementioned meaning and
  Z represents the grouping $>C=N-OH$ or $>CH-OH$
are reacted with halides of the formula

 Hal—R       (III)

in which
  R has the abovementioned meaning and
  Hal represents chlorine or bromine, if appropriate in the presence of a strong base and in the presence of a diluent.

If appropriate, an acid or a metal salt can be added onto the compounds of the formula (I) thus obtained.

Surprisingly, the compounds of the formula (I) according to the invention exhibit a better fungicidal activity than the substituted 1-benzyloximino- or -benzyloxy-1-phenyl-2-triazolyl-ethanes, such as, for example, 1-(4-chlorobenzyloximino)-1-(2,4-dichlorophenyl)-2-(1,2,4-triazol-1-yl)-ethane, 1-(2,6-dichlorobenzyloximino)-1-(2,4-dichlorophenyl)-2-(1,2,4-triazol-1-yl)-ethane or 1-(2-chlorobenzyloxy)-1-(2,4-dichlorophenyl)-2-(1,2,4-triazol-1-yl)-ethane, which are known from the prior art and are closely related compounds structurally and from the point of view of their action. The active compounds according to the invention thus represent an enrichment of the art.

Formula (I) provides a general definition of the substituted phenethyl-triazolyl derivatives according to the invention. Preferably, in this formula,
  $X^1$ and $X^2$, which can be identical or different, represent hydrogen, fluorine, chlorine, bromine or halogenoalkyl with 1 or 2 carbon atoms and 1 to 5 identical or different halogen atoms, such as, preferably, fluorine and chlorine, but $X^1$ and $X^2$ do not simultaneously denote hydrogen; and Y represents the grouping $>C=N-O-R$ or $>CH-O-R$ and
  R represents phenoxyethyl which is optionally mono-, di- or tri-substituted in the phenyl part by identical or different substituents, preferred substitutents which may be mentioned being: halogen and alkyl with 1 to 4 carbon atoms.

Particularly preferred compounds of the formula (I) are those in which
  $X^1$ and $X^2$ are identical or different and represent fluorine, chlorine or trifluoromethyl; and hydrogen if the other substituent does not represent hydrogen, and
  Y represents the grouping $>C=N-O-R$ or $>CH-O-R$, and
  R represents phenoxyethyl which is optionally mono-, di- or tri-substituted in the phenyl part by identical or different substitutents from the group comprising fluorine, chlorine and methyl.

Preferred compounds according to the invention are also addition products of acids and those substituted phenethyl-triazolyl derivatives of the formula (I) in which the substituents $X^1$, $X^2$, Y and R have the meanings which have already been mentioned as preferred for these substitutents.

Preferred acids which can be added on include hydrogen halide acids, such as, for example, hydrochloric acid and hydrobromic acid, in particular hydrochloric acid, and furthermore phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as p-toluenesulphonic acid and 1,5-naphthalenedisulphonic acid.

Other preferred compounds according to the invention are the addition products of salts and metals of main groups II to IV and sub-groups I and II and IV to VIII and those substituted phenethyl-triazolyl derivatives of the formula (I) in which the substituents $X^1$, $X^2$, Y and R have the meanings which have already been mentioned as preferred for these substituents.

Salts of copper, zinc, manganese, magnesium, tin, iron and nickel are particularly preferred here. Possible anions of these salts are those which are derived from acids which lead to physiologically acceptable addition products. In this connection, particularly preferred acids of this type are the hydrogen halide acids, such as, for example, hydrochloric acid and hydrobromic acid, and nitric acid and sulphuric acid.

If, for example, 1-(2,4-dichlorophenyl)-1-oximino-2-(1,2,4-triazol-1-yl)-ethane and 2,4-dichlorophenoxyethyl bromide are used as starting substances, the course of the reaction in the process according to the invention can be represented by the following equation:

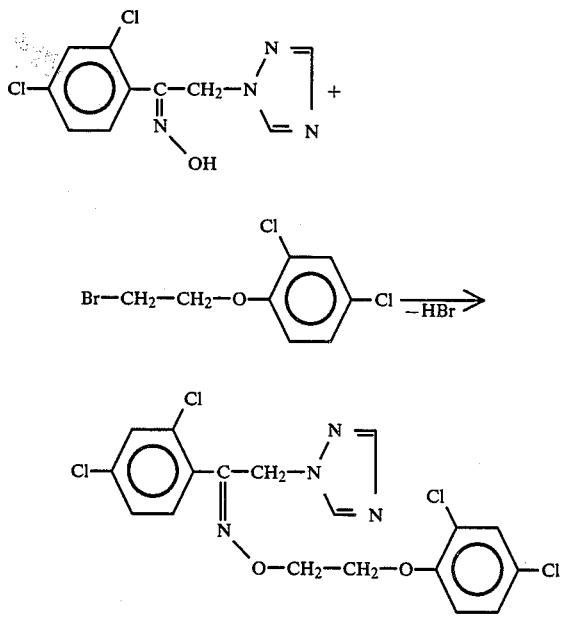

If, for example, 1-(2,4-dichlorophenyl)-2-(1,2,4-triazol-1-yl)-1-ethanol and 2,4-dichlorophenoxy-ethyl bromide are used as starting substances, the course of the reaction in the process according to the invention can be represented by the following equation:

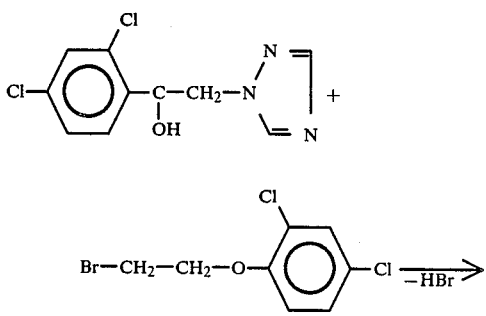

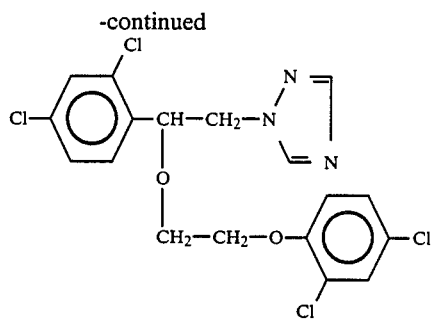

Formula (II) provides a general definition of the phenethyl-triazolyl derivatives required as starting substances in carrying out the process according to the invention. In this formula, $X^1$ and $X^2$ preferably have those meanings which have already been mentioned as preferred for these radicals in connection with the description of the substances of the formula (I) according to the invention.

The phenethyl-triazolyl derivatives of the formula (II) are known (compare German Offenlegungsschrift (German Published Specification) No. 2,431,407 and U.S. Pat. Nos. 4,327,104 and 4,357,338). They are obtained by reacting, in a first stage, ω-halogeno-acetophenones with 1,2,4-triazole in the presence of an inert organic solvent and in the presence of an acid-binding agent at temperatures between 20° and 120° C. and, in a second stage, either reducing the resulting ω-(1,2,4-triazol-1-yl)-acetophenones in a generally known manner with complex hydrides or with aluminum isopropylate, or reacting them with hydroxylamine, this compound preferably being employed as the hydrochloride in the presence of an acid-binding agent.

Formula (III) provides a general definition of the halides also to be used as starting substances for the process according to the invention. In this formula, R preferably represents those radicals which have already been mentioned as preferred for this substituent in connection with the description of the substances of the formula (I) according to the invention.

The halides of the formula (III) are generally known compounds of organic chemistry.

Possible diluents for the reaction according to the invention are inert organic solvents. Preferred solvents include, preferably, ethers, such as tetrahydrofuran and dioxane; aromatic hydrocarbons, such as toluene and benzene; and hexamethyl-phosphoric acid triamide, acid amides, such as dimethylformamide, and sulphoxides, such as dimethylsulphoxide.

If appropriate, the reaction according to the invention is carried out in the presence of a strong base. Preferred strong bases include alkali metal amides, hydrides, hydroxides and carbonates, such as, for example, sodium amide, carbonate, hydroxide or hydride and potassium amide, carbonate, hydroxide or hydride, and quaternary ammonium hydroxides and phosphonium hydroxides, such as, for example, tetramethylammonium hydroxide, benzyltrimethyl-ammonium hydroxide or dibenzyldimethylamminium hydroxide, and tetraphenylphosphonium hydroxide or methyltriphenylphosphonium hydroxide.

The reaction temperatures can be varied within a substantial range in the process according to the invention. In general, the reaction is carried out between 0° and 150° C., preferably at room temperature. In specific cases, it is advantageous to carry out the reaction at the boiling point of the solvent, for example between 60° and 100° C.

In carrying out the process according to the invention, 1 to 3 moles of halide of the formula (III) are preferably employed per mole of phenethyl-triazolyl derivative of the formula (II). The end products of the formula (I) are isolated in the generally known manner.

In a preferred embodiment of the process according to the invention, the reaction is carried out in a two-phase system, such as, for example, aqueous sodium hydroxide solution or potassium hydroxide solution/toluene, with addition of 0.01–1 mole of a phase transfer catalyst, such as, for example, ammonium or phosphonium compounds, the ethylates being formed in the organic phase or at the phase boundary and being reacted with the halides present in the organic phase.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

The metal salt complexes of the compounds of the formula (I) can be obtained in a simple manner by customary processes, thus, for example, by dissolving the metal salt in alcohol, for example ethanol, and adding the solution to compounds of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as against the powdery mildew of cereal causative organism (Erysiphe graminis) and the brown rust of wheat causative organism (Puccinia recondita), and furthermore for combating apple scab, powdery mildew on cucumbers and apples and rice diseases, such as Pellicularia.

When used in appropriate amounts, the active compounds according to the invention also exhibit insecticidal and plant growth-regulating properties.

The active compounds can be converted to the customary formulations, such as solutions, emulsions, wettable powders, suspensions, powders, dusting agents, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules or inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs and azo-metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

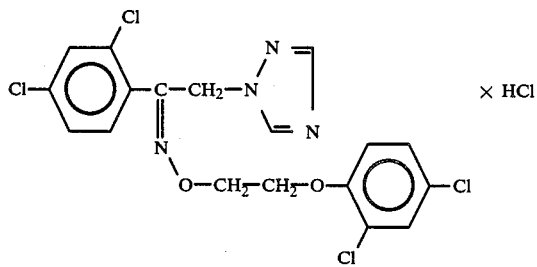

13.55 g (0.05 mole) of 1-(2,4-dichlorophenyl)-1-oximino-2-(1,2,4-triazol-1-yl)-ethane are dissolved in 100 ml of dimethylformamide, 7.0 g (0.05 mole) of potassium carbonate is first added, and 13.5 g (0.05 mole) of 2,4-dichlorophenoxy-ethyl bromide are then added dropwise. The reaction mixture is stirred at 40° to 60° C. for 48 hours. After it has cooled, it is stirred into 200 ml of saturated sodium chloride solution and the mixture is extracted with 100 ml of methylene chloride. The organic phase is washed with three 50 ml portions of water, dried over sodium sulphate and concentrated. The oily residue is dissolved in 100 ml of diethyl ether. Hydrogen chloride gas is then passed in until the solution is saturated, the mixture is concentrated by distilling off the solvent and the residue is taken up in 300 ml of diisopropyl ether. The crystals which precipitate are filtered off with suction. 6.6 g (26.6% of theory) of 1-(2,4-dichlorophenyl)-1-(2,4-dichlorophenoxy-ethoximino)-2-(1,2,4-triazol-1-yl)ethane hydrochloride of melting point 137°-38° C. are obtained.

Preparation of the Starting Substance

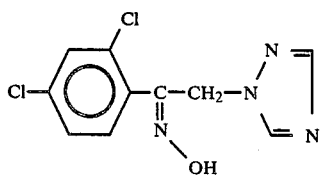

106.8 g (0.44 mole) of 1-(2,4-dichlorophenyl)-2-(1,2,4-triazol-1-yl)-1-ethanone are dissolved in 780 ml of ethanol, 48 g of hydroxylammonium hydrochloride are added and the mixture is heated under reflux for 5 hours. 1,000 ml of water are then added to the reaction mixture, and the mixture is filtered. 51 g (45% of theory) of 1-(2,4-dichlorophenyl)-1-oximino-2-(1,2,4-triazol-1-yl)-ethane of melting point 165°-170° C. are obtained.

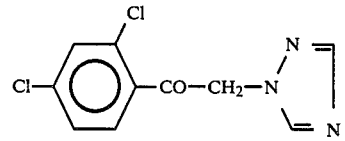

269 g (1 mole) of ω-bromo-2,4-dichloroacetophenone are dissolved in 250 ml of acetonitrile. This solution is added dropwise to a suspension, boiling under reflux, of 69 g (1 mole) of 1,2,4-triazole and 150 g of potassium carbonate in 2 liters of acetonitrile. After the mixture has been heated under reflux for 20 hours, the cooled suspension is filtered, the filtrate is freed from the solvent, the residue is taken up in ethyl acetate and the mixture is washed with water, dried over sodium sulphate and freed from the solvent. The ethyl acetate residue crystallizes out when isopropanol is added: after recrystallization from ligroin/isopropanol, 154 g (60% of theory) of 1-(2,4-dichlorophenyl)-2-(1,2,4-triazol-1-yl)-1-ethanone of melting point 117° C. are obtained.

EXAMPLE 2

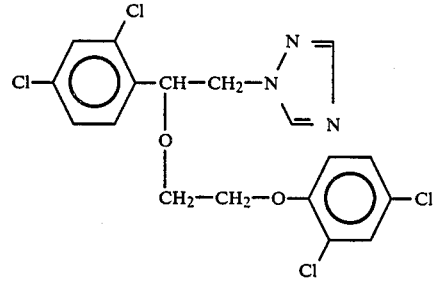

12.95 g (0.05 mole) of 1-(2,4-dichlorophenyl)-2-(1,2,4-triazol-1-yl)-1-ethanol are dissolved in 100 ml of toluene, and 100 ml of 40% strength sodium hydroxide solution and 1 ml of benzyl-dodecyl-dimethylammonium chloride are added. 13.5 g (0.05 mole) of 2,4-dichlorophenoxyethyl bromide are then added dropwise and the mixture is subsequently stirred at room temperature for 48 hours. The organic phase is separated off, washed with three 100 ml portions of saturated sodium chloride solution, dried over sodium sulphate and concentrated. The residue is taken up in 100 ml of diethyl ether, and crystallizes after the mixture has stood for a short time. 7.8 g (35% of theory) of 1-(2,4-dichlorophenyl)-1-(2,4-dichlorophenoxyethoxy)-2-(1,2,4-triazol-1-yl)-1-ethanol of melting point 88°-90° C. are obtained.

Preparation of the Starting Substance

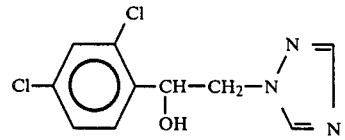

25.6 g (0.1 mole) of 1-(2,4-dichlorophenyl)-2-(1,2,4-triazol-1-yl)-1-ethanone are dissolved in 610 ml of methanol, and 6.3 g (0.15 mole) of sodium borohydride are added in portions at 5° to 10° C., while stirring. The mixture is then stirred at room temperature for one hour and heated at the boil for one hour. After the solvent has been distilled off, 250 ml of water and 50 ml of concentrated hydrochloric acid are added to the residue and the mixture is boiled up for 15 minutes. After the reaction mixture has been rendered alkaline with sodium hydroxide solution, the solid reaction product can be filtered off. It is recrystallized from aqueous acetonitrile. 12 g (42% of theory) of 1-(2,4-dichlorophenyl)-2-(1,2,4-triazol-1-yl)-1-ethanol of melting point 87° C. are obtained.

The following compounds of the general formula

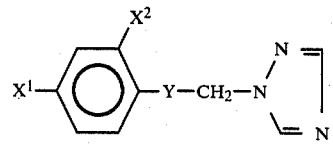

(I)

are obtained in a corresponding manner and according to the process described:

| Example No. | $X^1$ | $X^2$ | Y | Melting point (°C.) |
|---|---|---|---|---|
| 3 | Cl | Cl | >C=N—O—CH₂CH₂—O—(2,4,6-trichlorophenyl) | 73–75 |
| 4 | Cl | Cl | >C=N—O—CH₂CH₂—O—(4-chlorophenyl) | 128–30 (× HCl) |
| 5 | Cl | Cl | >C=N—O—CH₂CH₂—O—(4-methylphenyl) | 108–20 (× HCl) |
| 6 | Cl | Cl | >C=N—O—CH₂CH₂O—(2,4-dimethylphenyl) | 152–54 (× HCl) |
| 7 | Cl | CF₃ | >C=N—O—CH₂CH₂O—(2,4-dichlorophenyl) | 118–22 (× HNO₃) |
| 8 | Cl | CF₃ | >C=N—O—CH₂CH₂O—(4-chlorophenyl) | oil |
| 9 | Cl | CF₃ | >C=N—O—CH₂CH₂O—(2,4-dichlorophenyl) | oil |
| 10 | Cl | Cl | >CH—O—CH₂CH₂O—(2,4-dimethylphenyl) | 72–75 |

USE EXAMPLES

The compounds shown below are used as comparison substances in the use examples which follow:

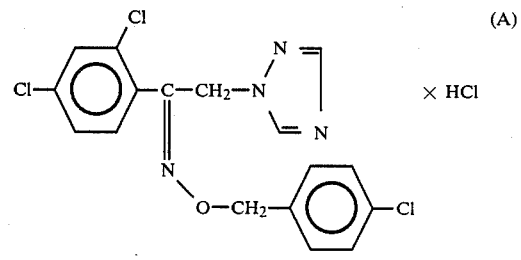

(A)

-continued (B) [chemical structure: 2,4-dichlorophenyl-CH(O-CH2-2-chlorophenyl)-CH2-N(triazole)]

(C) [chemical structure: 2,4-dichlorophenyl-C(=N-O-CH2-2,4-dichlorophenyl)-CH2-N(triazole) × HNO3]

EXAMPLE A

Erysiphe test (barley)/protective

Solvent: 100 parts by weight of dimethylformamide

Emulsifier: 0.25 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray-coating has dried on, the plants are dusted with spores of Erysiphe graminis f.sp. hordei.

The plants are placed in a greenhouse at a temperature of about 20° C. and a relative atmospheric humidity of about 80% in order to promote the development of mildew pustules.

Evaluation is carried out 7 days after the inoculation.

In this test, a clearly superior activity compared with the prior art is shown, for example, by the compounds according to the following preparation examples: 4, 5 and 2.

EXAMPLE B

Puccinia test (wheat)/protective

Solvent: 100 parts by weight of dimethylformamide

Emulsifier: 0.25 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of Puccinia recondita in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compounds according to the following preparation examples: 1, 5 and 2.

It will be appreciated that the instant specification and examples are set forth by way of illustration, and that various modifications and changes may be made without departing from the spirit and scope of the present invention.

What is claimed is:

1. A substituted phenethyl-triazolyl derivative of the formula

[chemical structure: $X^1$, $X^2$-substituted phenyl-Y-CH2-N(triazole)]

in which
$X^1$ and $X^2$ each independently is halogen or halogenoalkyl with 1 or 2 carbon atoms and 1 to 5 identical or different halogen atoms, and one of them may also be hydrogen,
Y is C=N—O—R, and
R is phenoxyethyl which is optionally mono-, di- or tri-substituted in the phenyl part by halogen and/or alkyl with 1 to 4 carbon atoms,
or an addition product thereof with an acid or salt.

2. A compound or addition product according to claim 1, in which
$X^1$ and $X^2$ each independently is fluorine, chlorine or trifluoromethyl, and one of them may also be hydrogen, and
R is phenoxyethyl which is optionally mono-, di- or tri-substituted in the phenyl part by fluorine, chlorine and/or methyl.

3. A compound according to claim 1, wherein such compound is 1-(2,4-dichlorophenyl)-1-(2,4-dichlorophenoxy-ethoximino)-2-(1,2,4-triazol-1-yl)-ethane of the formula

[chemical structure: 2,4-dichlorophenyl-C(=N-O-CH2-CH2-O-2,4-dichlorophenyl)-CH2-N(triazole)]

or an addition product thereof with an acid or metal salt.

4. A compound according to claim 1, wherein such compound is 1-(2,4-dichlorophenyl)-1-(2,4,6-trichlorophenoxy-ethoximino)-2-(1,2,4-triazol-1-yl)-ethane of the formula

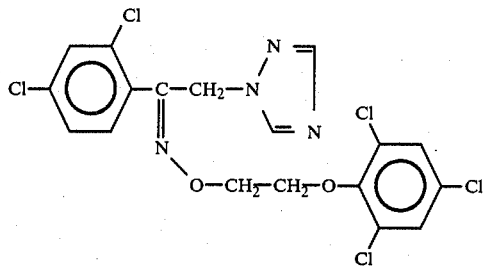

or an addition product thereof with an acid or metal salt.

5. A compound according to claim 1, wherein such compound is 1-(2,4-dichlorophenyl)-1-(4-chlorophenoxy-ethoximino)-2-(1,2,4-triazol-1-yl)-ethane of the formula

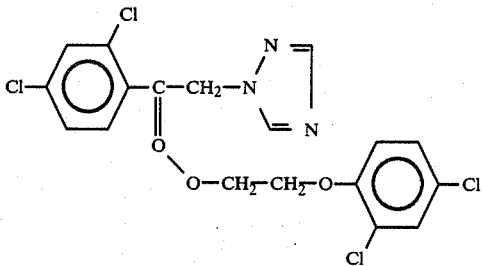

or an addition product thereof with an acid or metal salt.

6. A compound according to claim 1, wherein such compound is 1-(2,4-dichlorophenyl)-1-(4-methylphenoxy-ethoximino-2-(1,2,4-triazol-1-yl)-ethane of the formula

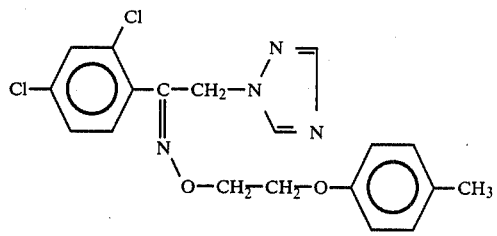

or an addition product thereof with an acid or metal salt.

7. A phytopathogenic fungicidal composition comprising a phytopathogenic fungicidally effective amount of a compound or addition product according to claim 1 in admixture with a diluent.

8. A method of combating phytopathogenic fungi which comprises administering to a plant of locus where a plant is to be grown a phytopathogenic fungicidally effective amount of a compound or addition product according to claim 1.

9. The method according to claim 8, wherein such compound is
1-(2,4-dichlorophenyl)-1-(2,4-dichlorophenoxy-ethoximino)-2-(1,2,4-triazol-1-yl)-ethane,
1-(2,4-dichlorophenyl)-1-(2,4,6-trichlorophenoxy-ethoximino)-2-(1,2,4-triazol-1-yl)-ethane,
1-(2,4-dichlorophenyl)-1-(4-chlorophenoxy-ethoximino)-2-(1,2,4-triazol-1-yl)-ethane or
1-(2,4-dichlorophenyl)-1-(4-methylphenoxy-ethoximino-2-(1,2,4-triazol-1-yl)-ethane, or an addition product thereof with an acid or metal salt.

10. A compound according to claim 1, in which
X$^1$ is hydrogen or chlorine, and
X$^2$ is hydrogen or chlorine, or is halogenoalkyl with 1 or 2 carbon atoms and 1 to 5 identical or different halogen atoms, but
X$^1$ and X$^2$ may not simultaneously represent hydrogen,
or an addition product thereof with hydrochloric acid or nitric acid.

* * * * *

UNITED STATES PATENT AND TRADEMARK OFFICE
CERTIFICATE OF CORRECTION

PATENT NO. : 4,771,065

DATED : September 13, 1988

INVENTOR(S) : Wolfgang Krämer, et al

It is certified that error appears in the above-identified patent and that said Letters Patent is hereby corrected as shown below:

| | |
|---|---|
| Col. 2, lines 31, 44, 49, 51 | Correct spelling of --substituents-- |
| Col. 12, line 60 and Col. 13, line 32 | Delete "  " and substitute 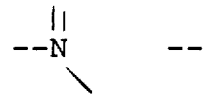 |
| Col. 13, line 35 | Bottom of formula delete "⁄Cl" |

Signed and Sealed this

Twenty-fifth Day of April, 1989

Attest:

DONALD J. QUIGG

Attesting Officer      Commissioner of Patents and Trademarks